United States Patent
Shoham et al.

(10) Patent No.: US 9,012,875 B2
(45) Date of Patent: Apr. 21, 2015

(54) INSPECTION METHOD AND AN INSPECTION SYSTEM EXHIBITING SPECKLE REDUCTION CHARACTERISTICS

(75) Inventors: Amir Shoham, Haifa (IL); Haim Feldman, Nof-Ayalon (IL); Doron Shoham, Rehovot (IL)

(73) Assignee: Applied Materials Israel, Ltd., Rehovot (IL)

(*) Notice: Subject to any disclaimer, the term of this patent is extended or adjusted under 35 U.S.C. 154(b) by 0 days.

(21) Appl. No.: 14/009,869

(22) PCT Filed: Apr. 7, 2011

(86) PCT No.: PCT/US2011/031629
§ 371 (c)(1),
(2), (4) Date: Nov. 26, 2013

(87) PCT Pub. No.: WO2012/138344
PCT Pub. Date: Oct. 11, 2012

(65) Prior Publication Data
US 2014/0299790 A1    Oct. 9, 2014

(51) Int. Cl.
*G01N 21/88* (2006.01)
*G01N 21/33* (2006.01)

(52) U.S. Cl.
CPC ............ *G01N 21/8806* (2013.01); *G01N 21/33* (2013.01); *G01N 2021/8822* (2013.01); *G01N 2201/0697* (2013.01)

(58) Field of Classification Search
CPC .................................................. G01N 21/8806
USPC ............. 250/227.12, 216, 492.22; 356/237.2, 356/237.5, 603, 604, 619
See application file for complete search history.

(56) References Cited

U.S. PATENT DOCUMENTS

| 4,660,980 A | 4/1987 | Takabayashi et al. |
| 2004/0099815 A1 | 5/2004 | Sfez et al. |
| 2005/0112474 A1 | 5/2005 | Sandstrom |
| 2006/0012802 A1* | 1/2006 | Shirley .......................... 356/603 |
| 2007/0013903 A1* | 1/2007 | Furman et al. ............. 356/237.5 |

(Continued)

FOREIGN PATENT DOCUMENTS

| JP | 2007147926 A2 | 6/2007 |
| JP | 2008277617 A2 | 11/2008 |
| WO | 2012/094011 A1 | 7/2012 |
| WO | 2012/138344 A1 | 10/2012 |

OTHER PUBLICATIONS

International Search Report of the International Searching Authority for International Application No. PCT/US2011/031629 mailed Jun. 27, 2011, 2 pages.

(Continued)

*Primary Examiner* — David Porta
*Assistant Examiner* — Meenakshi Sahu
(74) *Attorney, Agent, or Firm* — Kilpatrick Townsend & Stockton LLP (57) ABSTRACT

A method and an inspection system that exhibiting speckle reduction characteristics includes a light source arranged to generate input light pulses, and diffuser-free speckle reduction optics that include a beam splitter, for splitting an input light pulse from the light source into multiple light pulses that are oriented at angles in relation to each other when exiting the beam splitter, and at least one optical element for directing the multiple light pulses to impinge on an inspected object at different angles.

22 Claims, 11 Drawing Sheets

(56) References Cited

U.S. PATENT DOCUMENTS

| | | | |
|---|---|---|---|
| 2007/0121107 A1* | 5/2007 | Tsai et al. | 356/237.2 |
| 2007/0153393 A1* | 7/2007 | Chuang et al. | 359/619 |
| 2008/0165337 A1* | 7/2008 | Ershov et al. | 355/67 |
| 2009/0121157 A1 | 5/2009 | Moffatt et al. | |
| 2009/0201494 A1 | 8/2009 | Furman et al. | |
| 2009/0296758 A1 | 12/2009 | Brown et al. | |
| 2010/0097680 A1* | 4/2010 | Naftali et al. | 359/205.1 |
| 2010/0163757 A1 | 7/2010 | Joobeur et al. | |
| 2010/0265466 A1 | 10/2010 | Lescure et al. | |
| 2014/0036942 A1 | 2/2014 | Vander et al. | |

OTHER PUBLICATIONS

International Search Report and Written Opinion of the International Searching Authority for Application No. PCT/US2011/020424, mailed on Mar. 11, 2011, 8 pages.

International Preliminary Report on Patentability for International Application No. PCT/US2011/031629 mailed Oct. 17, 2013, 7 pages.

International Preliminary Report on Patentability for International Application No. PCT/US2011/020424 mailed Jul. 18, 2013, 8 pages.

* cited by examiner

INSPECTION METHOD AND AN INSPECTION SYSTEM EXHIBITING SPECKLE REDUCTION CHARACTERISTICS

CROSS-REFERENCE TO RELATED APPLICATIONS

This application is a U.S. National Stage of PCT Application No. PCT/US 2011/031629, filed Apr. 7, 2011, the entire contents of which are incorporated herein by reference in their entirety for all purposes.

BACKGROUND

Current demands for high density and performance associated with ultra large scale integration in semiconductor devices require submicron features, increased transistor and circuit speeds, and improved reliability. Such demands require formation of device features with high precision and uniformity, which in turn necessitates careful process monitoring.

Known inspection techniques typically use imaging the articles with a large magnification on to a charge-coupled device (CCD) camera. The imaging technique requires the article to be illuminated. The brightness of the illuminating source is a key factor in the ability to speed the inspection by reducing the integration time of camera. As the patterns on wafers get smaller, it becomes necessary to use shorter wavelengths in order to be able to detect the patterns. This is due to the fact that the physical resolution limit depends linearly on the illumination wavelength and due to interference effects which require that the inspection be done at a wavelength similar to the one used in the lithographic process.

As the wavelengths get smaller, conventional incoherent light sources like filament lamps or gas discharge lamps do not have sufficient brightness, and the light sources of choice become short wavelength lasers. The coherence of the laser, together with the roughness and aberrations of the surfaces as well as the patterned article along the light path, creates an artifact known as speckle, which is a noisy pattern over the image of the article.

Speckle causes problems in detection of the surfaces of articles being inspected and causes false alarms because of the non uniformity of the light pattern hitting the detector. Detection accuracy is degraded. Also, images taken of inspected articles are degraded. The problem is an acute one in this type of article inspection, because the power provided by coherent light is essential, among other reasons, as a result of losses stemming from the detection process.

U.S. Pat. Nos. 7,463,352, 7,133,548, 6,924,891, 6,798, 505, 6,587,194, 6,556,294, 6,466,315, 6,429,931, 6,369,888 and 6,268,093. all being incorporated herein by reference. provide some state Of the art speckle reduction methods and systems.

U.S. Pat. No. 7,449,673 discloses a system and a method for speckle reduction. It discloses, for example. a diffuser based solution. Diffusers are known to introduce their own speckle and complicate the speckle reduction solution.

When operating in the Ultra Violet (UV) region, and especially the deep Ultra Violet (DUP) region, the cost of optical components increases and various prior art speckle reduction solutions are either too expensive or inefficient.

As can be appreciated from the foregoing discussion, there is a need in the art for a method and system fir reducing speckle when inspecting articles using pulsed laser pulses at low wavelengths, including the deep UV region.

SUMMARY

According to an embodiment of the invention an inspection system may be provided. The inspection system may exhibit speckle reduction characteristics, and may include: (a) a light source arranged to generate input light pulses (that may be of an ultra violet radiation), and (b) diffuser-free speckle reduction optics. The diffuser-free speckle reduction optics may include (b.1) a beam splitter for splitting an input light pulse from the light source to multiple light pulses that are oriented in relation to each other when exiting the beam splitter; and (b.2) at least one optical element for directing the multiple pulses to impinge on an inspected object at different angles.

The at least one optical element may include a delay modulator introducing a delay between each of the multiple light pulses.

The delay module may be arranged to introduce a delay that is longer that a width of the input light pulse.

The delay module may be arranged to introduce a delay that is longer that a coherence length of the input light pulse.

The light source may be a single mode laser.

The beam splitter may be an acousto-optic device that is arranged to split the input light beam to provide multiple light beams while introducing a frequency shift between the multiple light pulses.

The beam splitter may be an acousto-optic device that is modulated by a sinusoidal modulation signal.

Each of the multiple light pulses, when impinging on the inspected object, may have an elongated cross section. The shape of the cross section may differ from a square.

The longitudinal axis of the elongated cross section may be perpendicular to a direction of propagation of at least one of the multiple light pulses.

The system may include collection optics fir collecting scattered light from the inspected object.

The system may include a sensor that may be arranged to receive scattered light while being prevented from receiving reflected light from the inspected object. A sensor of the system may include various portions of scattered and reflected light.

The diffuser-free speckle reduction optics may have an illumination axis that may differ from the collection axis of the collection optics. The projections of these axes on the inspected object May be oriented in relation to each other.

The diffuser-free speckle reduction optics may be arranged to direct different light pulses, located within an illumination angular zone, towards the inspected object. The system may include collection optics for collecting light that propagates through a collection angular zone that differs from the illumination angular zone.

The illumination angular zone may be surrounded by the collection angular zone.

The multiple light pulses may include an even number of light pulses or an odd number of light pulses.

According to an embodiment of the invention an inspection method, may be provided. The method may include: (a) generating an input light pulse (that may be of ultra violet radiation); (b) splitting, by a beam splitter of a diffuser-free speckle reduction optics, the input light pulse multiple light pulses that are oriented in relation to each other when exiting the beam splitter; and (c) directing, by at least one optical element of the diffuser-free speckle reduction optics, the multiple pulses to impinge on an inspected object at different angles.

The method may include introducing a delay between each a the multiple light pulses before the multiple light pulses impinges in the inspected object.

The method may include introducing a frequency shift between each of the multiple light pulses by an acousto-optic device.

The method may include shaping the input light pulse to have an elongated cross section so that each of the multiple light pulses, when impinging on the inspected object, has an elongated cross section that has a shape that differs from a square; wherein a longitudinal axis of the elongated cross section may be oriented in relation to a direction of propagation of the light pulse.

The method may include directing the multiple light pulses towards the inspected object while the multiple light pulses are located within an illumination angular zone; and collecting light that propagates through a collection angular zone that differs from the illumination angular zone.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, element shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

According to an embodiment of the invention an inspection system is provided. It may operate in the ultra violet region and can direct multiple light pt having durations of nanoseconds towards an inspected object.

The inspection system does not utilize a diffuser and can reduce speckle by directing multiple light pulses towards an inspected object so as to impinge on the inspected object at different angles.

The multiple (discrete) light pulses that impinge on the inspected object at different directions have substantially the same effect as illuminating the inspected object with a large beam that is delimited by angle that is defined by the most distant light pulses. The multiple light beams provide a "virtual" illumination path numerical aperture that equals a large fraction of a collection numerical aperture obtained by illuminating the object with the large beam.

The inspection system can further reduce speckle by delaying the multiple light pulses in relation to each other and additionally or alternatively, by introducing a frequency shift between the multiple light pulses.

It has been found that illuminating an inspected object by multiple discrete light pulses that have different incidence angles can provide a "virtual" illumination module numerical aperture that is responsive to a maximal angular difference between the incidence angles of the light pulses. The numerical aperture of the illumination can be equal to the sine of that maximal angular difference. Referring to the example set forth in FIGS. 1-4, the numerical aperture of illumination is responsive to the angle between light beams 12 and 14 when impinging on the inspected object.

Figure 1:
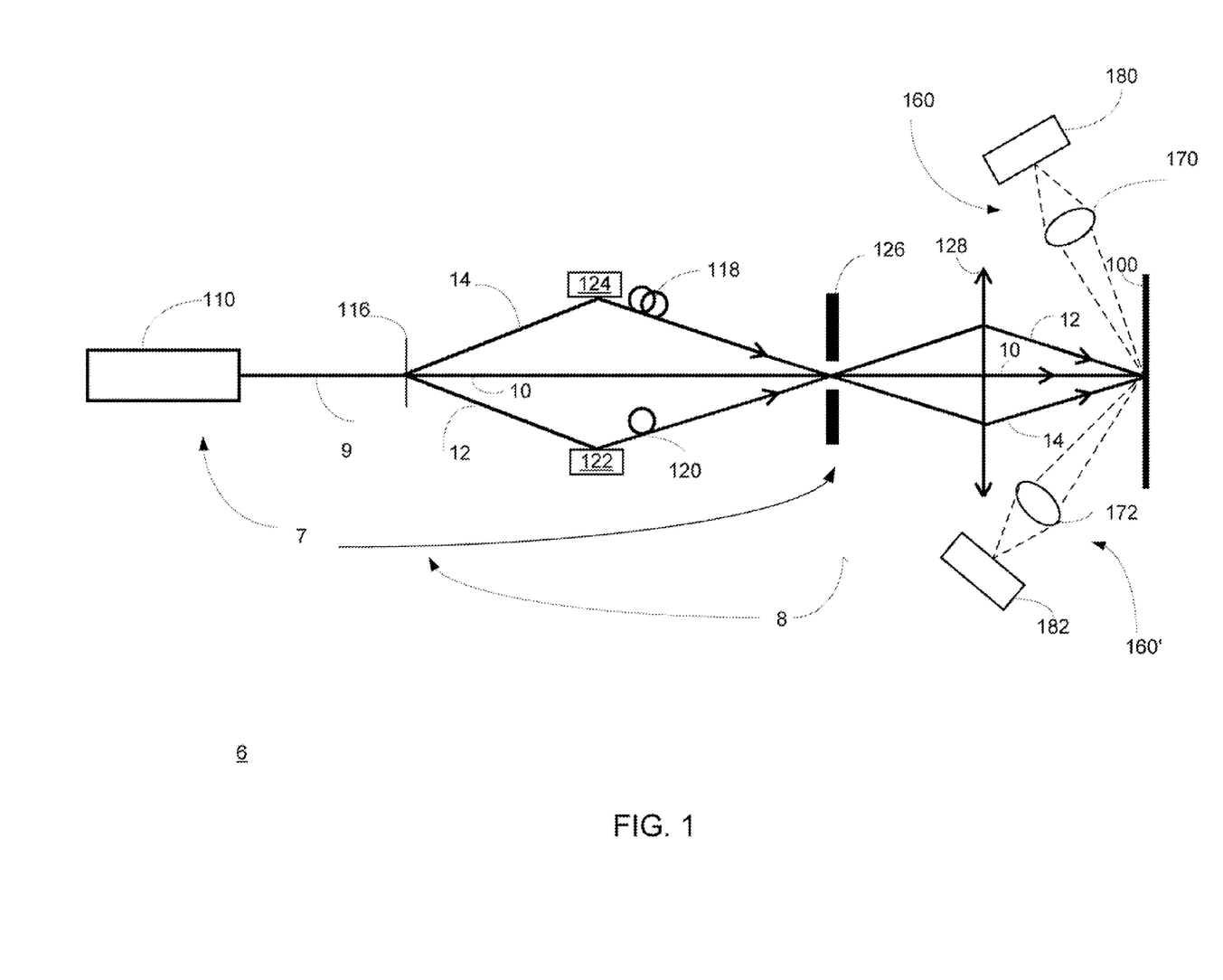
FIG. 1 illustrates an illumination module and two collection modules of an inspection system according to an embodiment of the invention.

FIG. 1 illustrates an inspection system 6 that includes: (a) an illumination module 7 that includes a light source 110 and diffuser-free speckle reduction optics 8, and (b) two collection modules 160 and 160', according to an embodiment of the invention.

The light source 110 is arranged to output light pulses of ultra violet radiation, and even deep ultra violet radiation. The duration of each pulse is in the nanosecond region—e.g., a few nanoseconds, a few tens of nanoseconds and the like. The light source 110 outputs so called input light pulses. These light pulses are termed "input light pulses" merely to indicate that they are input to the diffuser-flee speckle reduction optics 8 and in order to make a distinction between the input light pulses and the multiple light pulses generated by the diffuser-free speckle reduction optics 8.

The diffuser-free speckle reduction optics 8 splits an input light pulse into multiple light pulses. These multiple light pulses propagate in different directions oriented in relation to each other. Despite the different directions in which these multiple light pulses propagate, the diffuser-free speckle reduction optics 8 can have an illumination axis.

The illumination axis of the diffuser-free speckle reduction optics 8 can be defined by any one of the following:
 a. The direction of propagation of the input light pulse that enters the diffuser-free speckle reduction optics 8;
 b. The direction of propagation of a shortest path light pulse out of the multiple light pulses that propagates through the diffuser-free speckle reduction optics 8;
 c. The direction of propagation of a light pulse (out of the multiple light pulses) that is located at the center of the others of the multiple light pulses; or d. An average angle of incidence of the all the multiple light pulses that impinge on the inspected object.

The diffuser-free speckle reduction optics 8 is diffuser-free in the sense that it does not include a diffuser or at least does not use a diffuser to reduce speckle.

The inspection system 6 can include additional components such as an image processor, controller, mechanical stage, power supply module, and the like. For simplicity of explanation these components are not shown in detail in the drawings.

FIG. 1 illustrates diffuser-free speckle reduction optics 8 as having an illumination axis (an imaginary horizontal axis) that is oriented at an angle to the collection axis of each of the collection modules 160 and 160'. It is noted that this can be regarded as a dark field configuration in which the collection modules 160 and 160' collect scattered light while not collecting reflected light. It is noted that the inspection system 6 can have other configurations in which sensors of the collection modules collect other combinations of scattered light and reflected light. For example, the inspection system 6 can operate in a bright field configuration.

Although FIG. 1 illustrates two collection modules, the system can include one or more than two collection modules.

FIG. 1 illustrates diffuser-tree speckle reduction optics 8 as being arranged to receive an input light pulse 9, which is split (by beam splitter 116) to multiple (three) light pulses 10, 12 and 14 that exit the beam splitter 116 while being oriented at angles to each other.

Light pulse 10 propagates along the illumination axis of the diffuser-free speckle reduction optics 8, light pulse 12 propagates to form a negative angle in relation to the illumination axis and light pulse 14 propagates to form a positive angle in relation to the illumination axis.

The number of pulses can differ from three, and the different light pulses can propagate in a symmetrical manner (as illustrated in FIG. 1) or in an asymmetrical manner in relation to each other.

Light pulse 14 propagates towards an upper reflector 124 that directs the light pulse 14 at a negative angle so as to pass through an aperture of a beam stop 126.

Light pulse 12 propagates towards as lower reflector 124 that directs the light pulse 12 at a positive angle to such as to pass through the aperture of the beam stop 126.

The paths of light pulses 10, 12 and 14 may intersect at the beam stop 126 (or in proximity to the aperture of the beam stop) and this intersection may be imaged by objective lens 128 onto the inspected object so that the three light pulses 10, 12 and 14 impinge on the inspected object at different incidence angles. FIG. 1 illustrates the light pulse 12 as impinging at a negative incidence angle (in relation to the illumination axis), light pulse 14 as impinging at a positive incidence angle (in relation to the illumination axis) and light pulse 10 impinging in parallel to the illumination axis.

FIG. 1 also illustrates collection modules 160 and 160' as being located in a symmetrical manner on both sides of the illumination axis.

Collection module 160 includes collection optics 170 and sensor 180. Collection module 160' includes collection optics 172 and sensor 182. The collection optics 170 and 172 are illustrated as a single objective lens but other or additional optical components can be used. The sensors can be array sensors, CCD sensors, or any other commercially available sensor.

FIG. 1 also illustrates a first delay unit 118 a second delay unit 120 that form a delay module.

The first delay unit 118 delays light pulse 14 and the second delay unit 120 delays light pulse 12. These delay units (118, 120) can delay light pulses 10 and 12 and 14 in relation to each other. The delay between each light pulse of the multiple light pulses should be longer than the coherence length of the light source 110.

The delay introduced between each of the light pulses 10, 12 and 14 can be longer than the pulse width of each of these light pulses, but may be shorter than the pulse width but longer than the mentioned above coherence length. The introduction of such a delay further reduces speckles.

Figure 8:
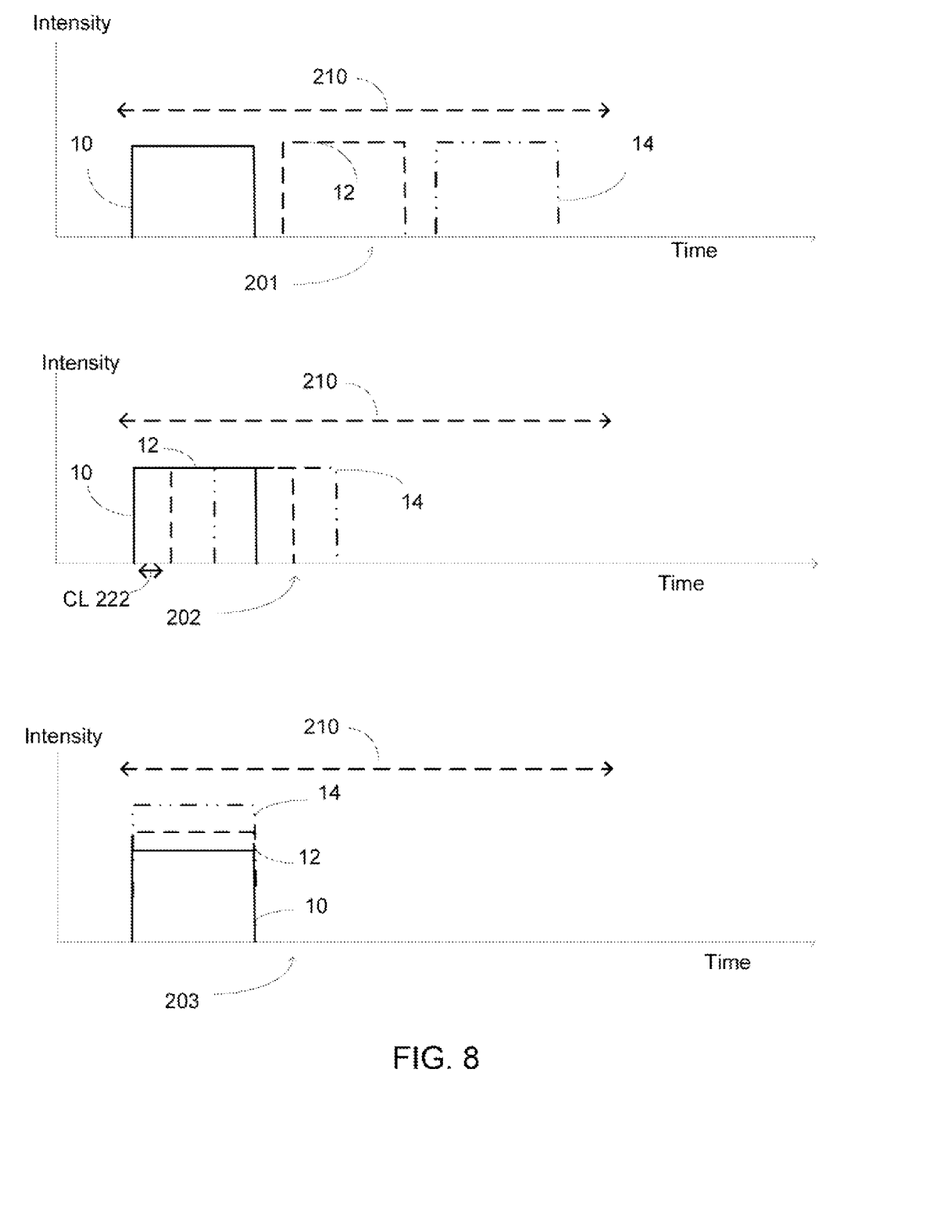
FIG. 8 is a timing diagram according to an embodiment of the invention.

Referring to the example set forth in FIG. 8, graph 201 illustrates non-overlapping light pulses 10, 12 and 14, that arrive within a sensing period 210 of a sensor. This non-overlap is contributed by the delay applied by delay units 118 and 120.

Graph 202 illustrates partially overlapping pulses 10, 12 and 14 that arrive within the sensing period 210. The pulses 10, 12 and 14 are delayed in relation to each other by a delay that is longer than the coherence length (denoted CL 222) of the light source 110.

Figure 3:
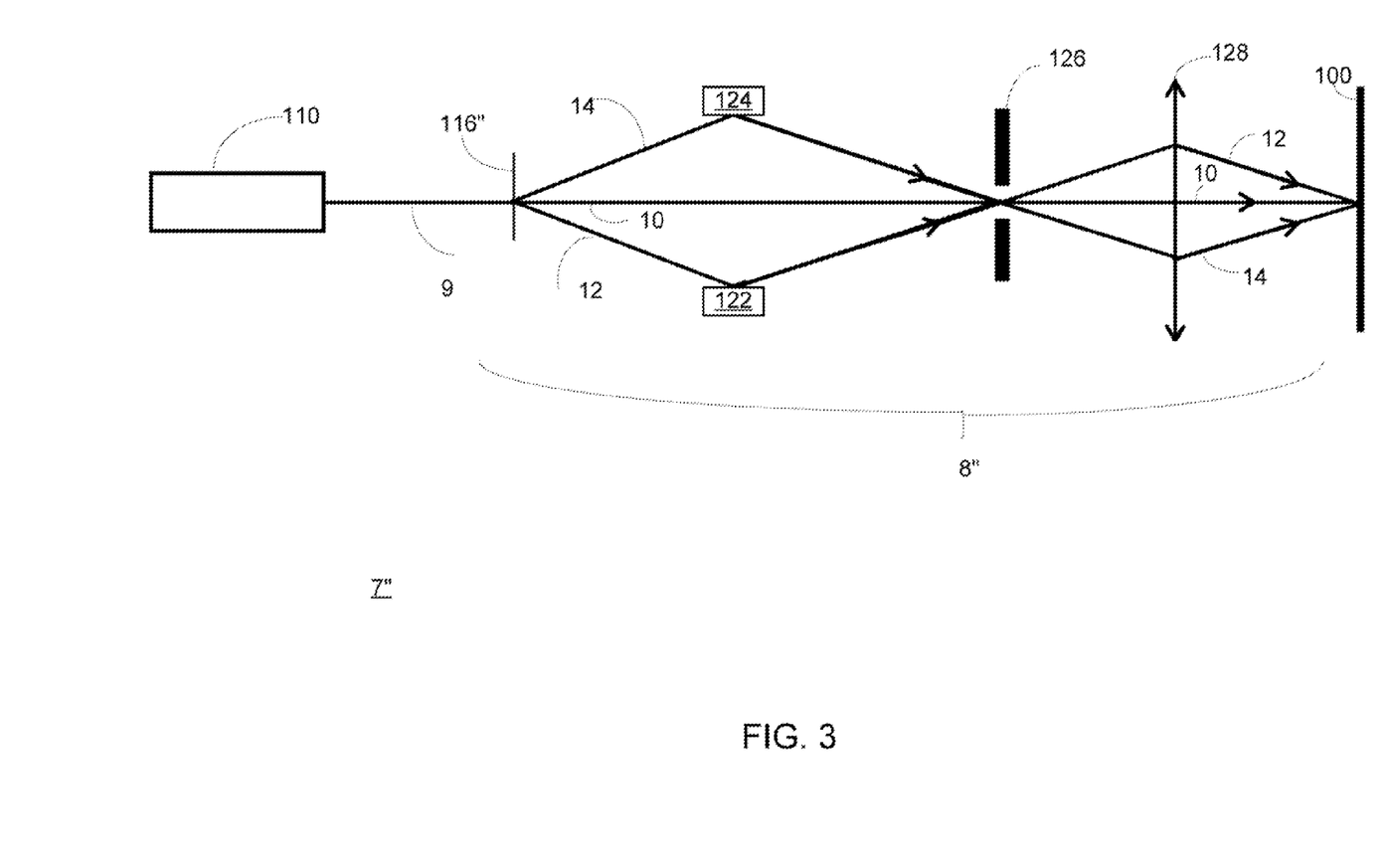
FIG. 3 illustrates an illumination module of an inspection system according to an embodiment of the invention.
Figure 4:
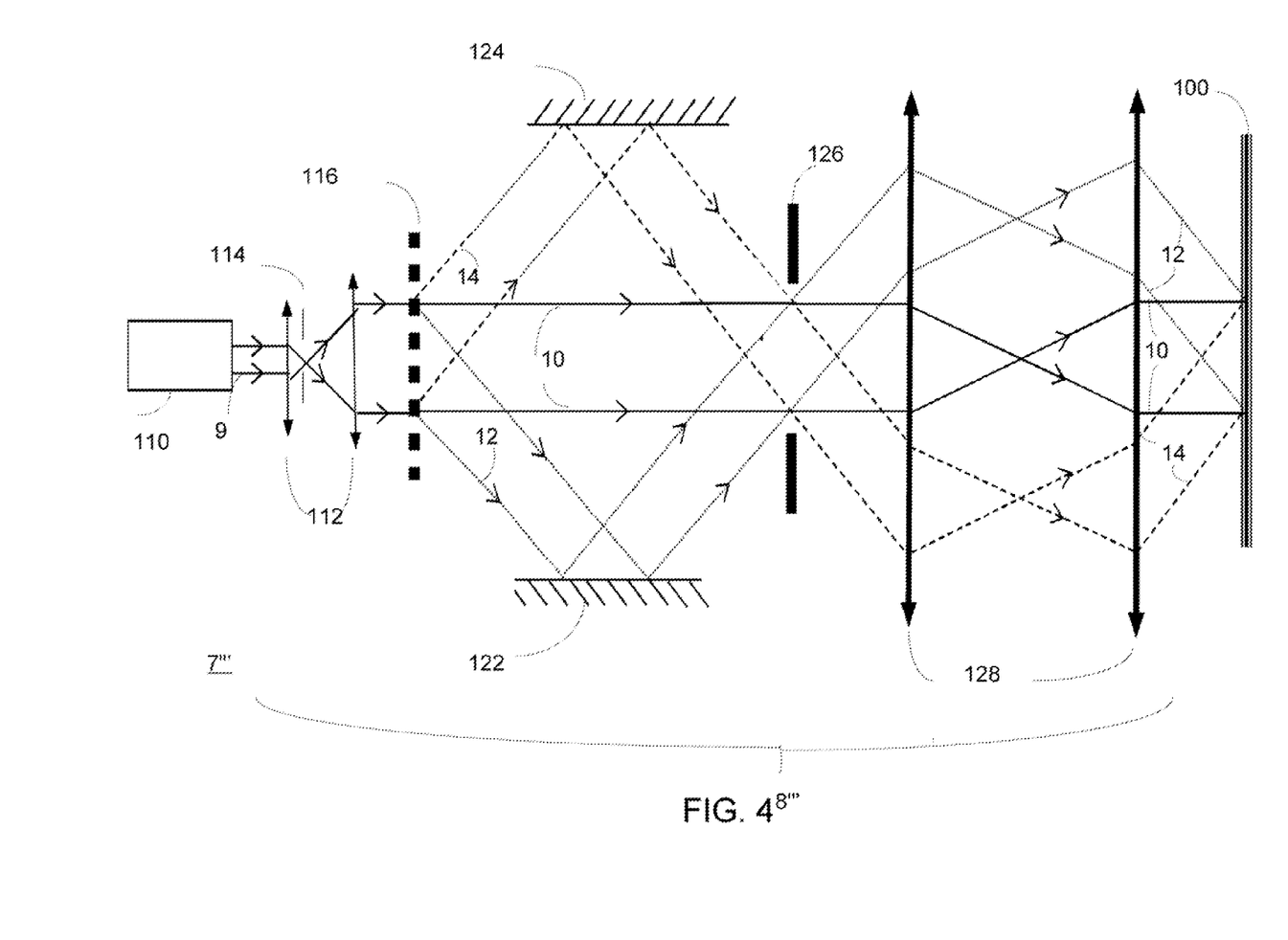
FIG. 4 illustrates an illumination module of an inspection system according to an embodiment of the invention.

Graph 203 illustrates fully overlapping pulses 10, 12 and 14 that are frequency shifted in relation to each other, wherein this frequency shift can be introduced by the illumination modules of FIGS. 3 and 4. It is noted that the intensities of light pulses 10 12 and 14 were illustrated, in graph 203, as being different from each other in order to emphasize that there are three different light pulses. In fact, the intensities of the three light pulses can be equal to each other or substantially equal.

It is noted that in any of the mentioned above eases the intensities of the light pulses can differ from each other or may be the same. In order to equalize the intensity of the light pulses once impinging on the inspected object these light pulses (or at least some of the light pulses) can pass through attenuators (or other gain affecting units).

Figure 2:
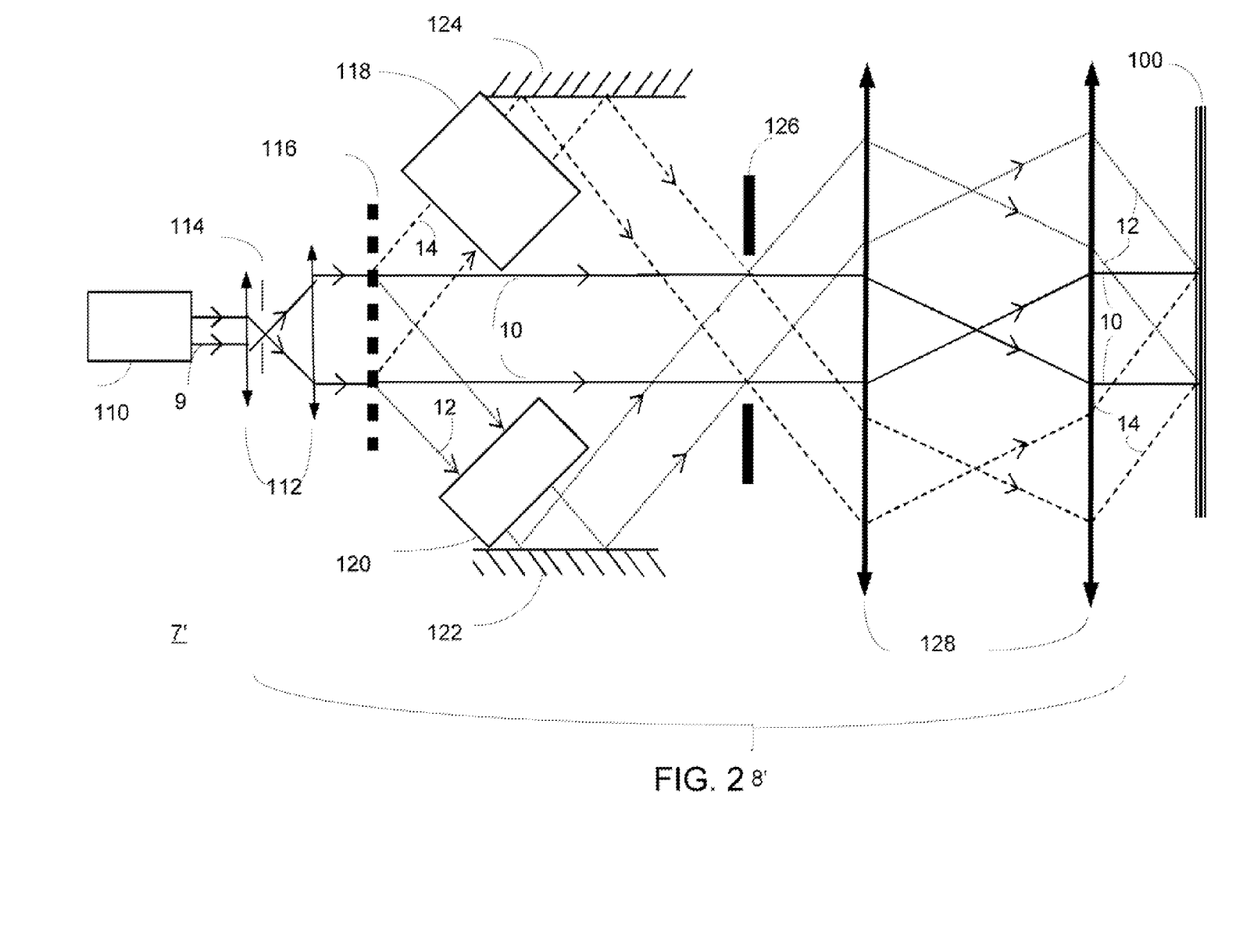
FIG. 2 illustrates an illumination module of an inspection system according to an embodiment of the invention.

FIG. 2 illustrates an illumination module 7' of an inspection system according to an embodiment of the invention.

The illumination module 7' includes a light source 110 and diffuser-free speckle reduction optics 8'.

Diffuser-free speckle reduction optics 8' of FIG. 2 differs from the diffuser-free speckle reduction optics 8 of FIG. 1 by including a spatial filter 114, beam expanding lenses 112 and two imaging lenses 128.

In addition, in FIG. 2 each light pulse out of light pulses 9, 10, 12 and 14 are illustrated by two parallel arrows (and not a single arrow as illustrated in FIG. 1) that better illustrate the shape of the input light pulse and the multiple light pulses.

Diffuser-free speckle reduction optics 8' includes a spatial filter 114 that is positioned between the two beam expanding lenses 112. The two beam expanding lenses 112 and the spatial filter 114 are positioned between the light source 110 and the beam splitter 116. The two beam expanding lenses expand the input light pulse before it enters the beam splitter 116.

The spatial filter 114 may perform any type of spatial filtering. It can, for example include an aperture that passes only single mode elements of light generated by a non-ideal single mode laser.

The beam splitter 116 can be a grating but this is not necessarily so.

FIG. 3 illustrates an illumination module 7" of an inspection system according to an embodiment of the invention.

The illumination module 7" includes light source 110 and diffuser-free speckle reduction optics 8". Diffuser-free speckle reduction optics 8" differs from diffuser-free speckle reduction optics 8 of FIG. 1 by lacking a delay module and by having an acousto-optic modulator 116" instead of beam splitter 116.

FIG. 3 illustrates diffuser-free speckle reduction optics 8" as being arranged to receive an input light pulse 9 and split by an acousto-optic modulator 116" to multiple (three) light pulses 10, 12 and 14 that exit the acousto-optic modulator 116" while being oriented in relation to each other and while being frequency shifted in relation to each other. The frequency shift should be such that there are a sufficient number of cycles of it during the pulse. This will allow elimination of the interference between the pulses. The introduction of the frequency shift can be obtained by feeding a sinusoidal wave to the acousto-optic modulator 116". The frequency shift prevents or at least substantially reduces speckle and thus the diffuser-free speckle reduction optics 8" can be free of delay units. The introduction of delay or frequency shift may prevent interference between the different light pulses. The delay should be larger than the coherence length, and the frequency shill should be such that there are enough cycles of the different frequencies within the duration of the light pulse.

It is noted that diffuser-free speckle reduction optics can include both an acousto-optic modulator 116' and delay units 118 and 120 for further reducing speckle.

FIG. 4 illustrates an illumination module 7''' of an inspection system according to an embodiment of the invention.

The illumination module 7''' includes light source 110 and diffuser-free speckle reduction optics 8'''.

Diffuser-free speckle reduction optics 8''' differs from the diffuser-free speckle reduction optics 8" of FIG. 3 by including a spatial filter 114, beam expanding lenses 112 and two imaging lenses 128.

In addition, each light pulse out of light pulses 9, 10, 12 and 14 is illustrated by two parallel arrows (and not a single arrow) that better illustrate the shape of light pulses that propagate through diffuser-free speckle reduction optics 8''' and are directed towards the inspected object 100 at different angles.

Diffuser-free speckle reduction optics 8" includes a spatial filter 114 that is positioned between the two beam expanding lenses 112. The two beam expanding lenses 112 and the spatial filter 114 are positioned between the light source 110 and the acousto-optic modulator 116. The two beam expanding lenses expand the input light pulse before it enters the acousto-optic modulator 116.

Figure 5:
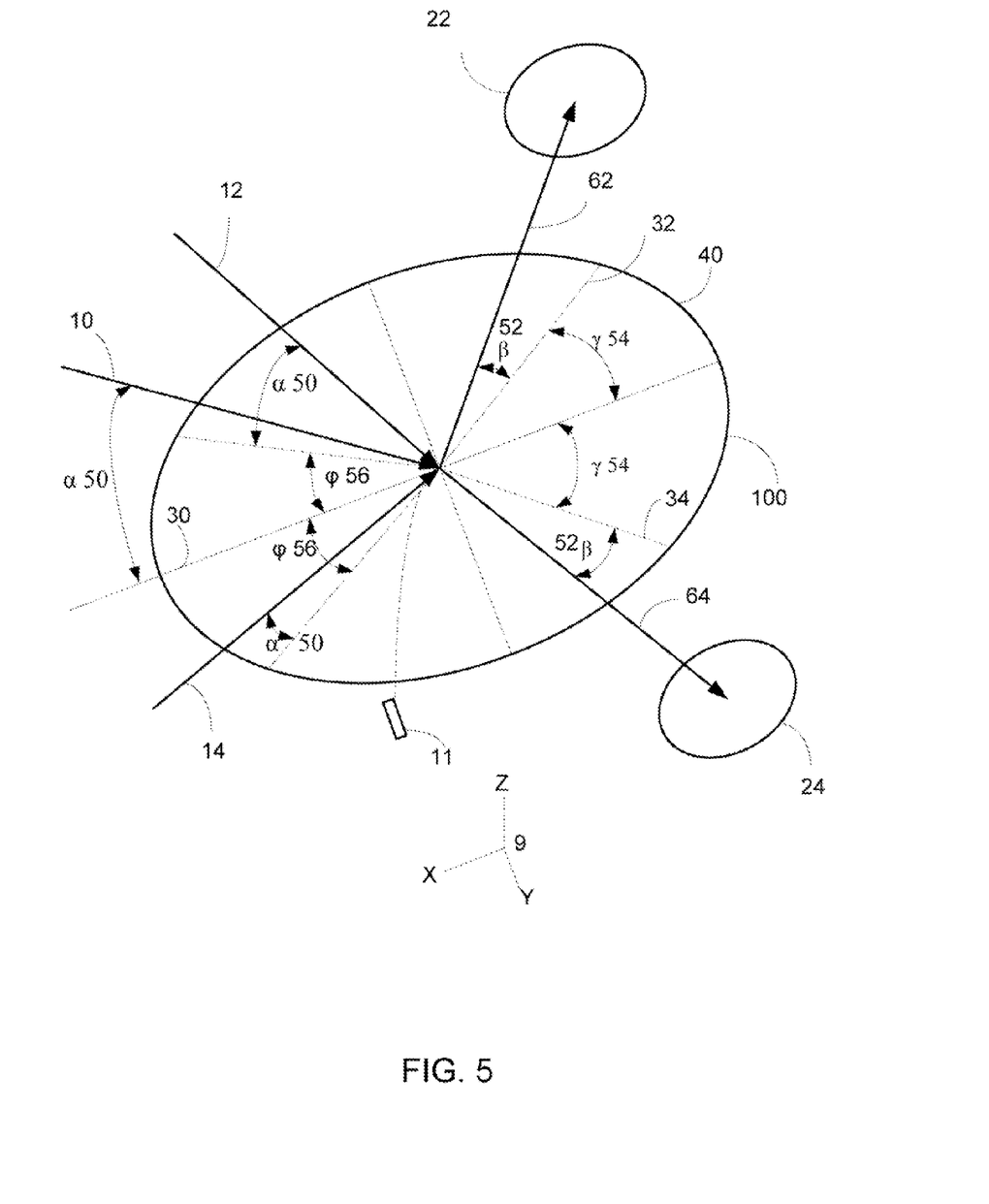
FIG. 5 illustrates a relationship between illumination angles, collection angles and collection angular zones according to an embodiment of the invention.

FIG. 5 illustrates a relationship between illumination angles, collection angles and collection angular zones according to an embodiment of the invention.

Each of light pulses 10, 12 and 14 propagates along a path that is oriented, in relation to the plane of the inspected object 100, by an angle denoted alpha ($\alpha$) 50.

The paths of light pulses 10, 12 and 14 are also oriented in relation to each other—as illustrated by angle phi ($\phi$) 56 that is defined between the projection of these paths at the plane of the inspected object 100.

The projection 30 of the path of light pulse 10 on the plane of the inspected object is oriented at an angle of phi ($\phi$) 56 in relation to the projection of the path of each of light pulses 12 and 14 at on the plane of the inspected object. Light pulse 10 propagates along an illumination axis of the illumination module 7.

FIG. 5 illustrates collection modules 160 and 160' as having collection angles defined by collection axes 62 and 64. The collection modules 160 and 160' are positioned such as to collect scatter light (within collection angular ranges 22 and 24) while not collecting reflected light from the inspected object 100.

Collection axes 62 and 64 are oriented by an angle beta ($\beta$) 52 in relation to the plane of the inspected object and are oriented by an angle gamma ($\gamma$) 54 in relation to the projection 30 of the path of the first light pulse 10.

The values of each of these angles (alpha, beta, gamma and phi) can differ from those illustrated in FIG. 5. Non-limiting examples may include alpha of sixty five degrees, gamma of forty live degrees, phi of twenty degrees, beta of thirty degrees and the like.

The relationship between these angles may determine the amount of scattered light and, additionally or alternatively, reflected light that can be gathered by the sensors of the inspection system.

FIG. 5 also illustrates light pulses 10, 12 and 14 as having, when impinging on the inspected object, an elongated cross section 11. The cross section 11 has a shape that differs from a square. A longitudinal axis of the elongated cross section 11 is illustrated as being perpendicular to path of the light pulse 10. It can be oriented in other angles to the direction of propagation of the light pulse.

Figure 6:
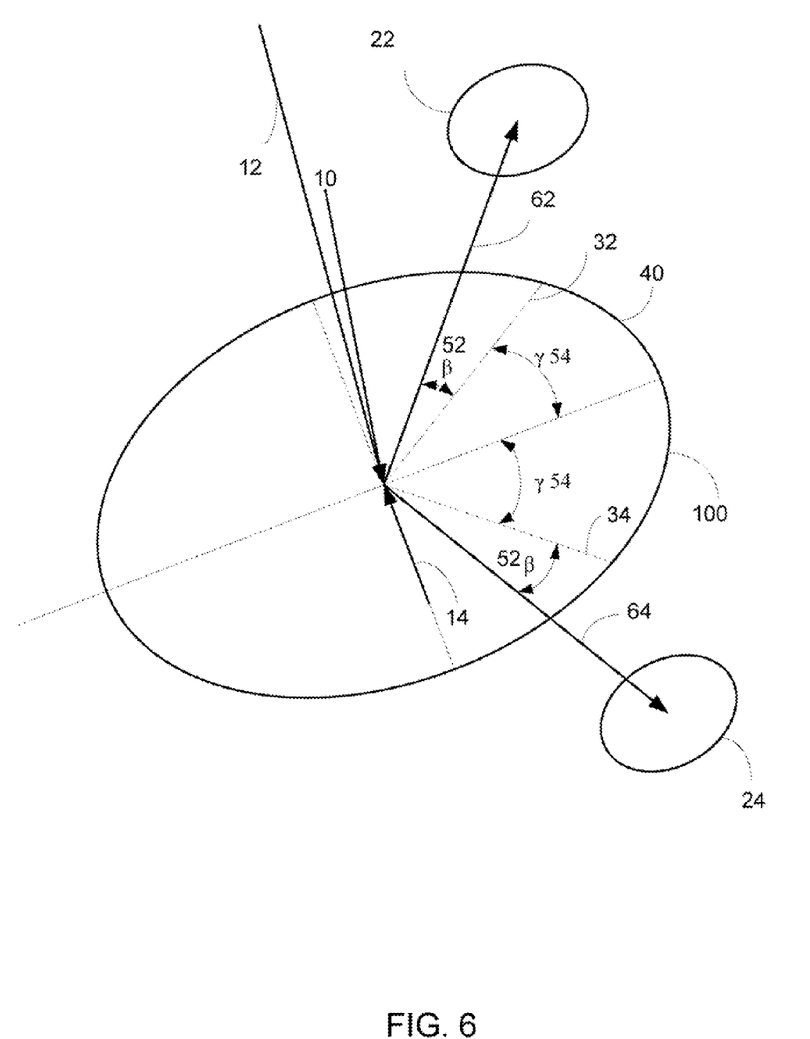
FIG. 6 illustrates a relationship between illumination angles, collection angles and collection angular zones according to an embodiment of the invention.

FIG. 6 illustrates a relationship between illumination angles, collection angles and collection angular zones according to an embodiment of the invention.

FIG. 6 differs from FIG. 5 by the angle of incidence of light pulses 10, 12 and 14. These light pulses propagate in paths that are normal to the plane of the inspected object 100. In other words, alpha equals ninety degrees.

Figure 7:
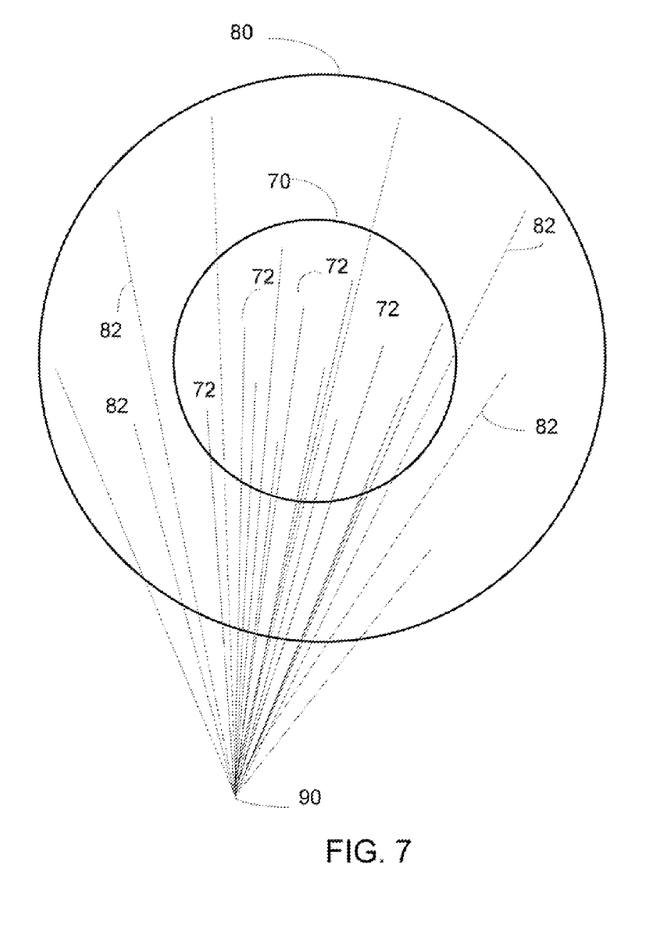
FIG. 7 illustrates a relationship between a collection angular zone and an illumination angular zone according to an embodiment of the invention.

FIG. 7 illustrates a relationship between as collection angular zone 80 and an illumination angular zone 70 according to an embodiment of the invention.

Any of the mentioned above diffuser-free speckle reduction optics 8, 8', 8" or 8''' can be arranged to direct different light pulses towards the inspected object 100 at different angles. These different light pulses (denoted 72 in FIG. 7) are located within an illumination angular zone 70. The collection optics (such as collection modules 160 and 160') can be arranged to collect light that propagates within one or more so-called collection angular zones.

FIG. 7 illustrates a collection angular zone 80 that differs from the illumination angular zone 70. Furthermore, FIG. 7 illustrates an illumination angular zone 70 that is surrounded by the collection angular zone 80. Collected light pulses are denoted 82. It is noted that such zones can be implemented by using annular mirrors, annular reflectors, and the like.

Figure 9:
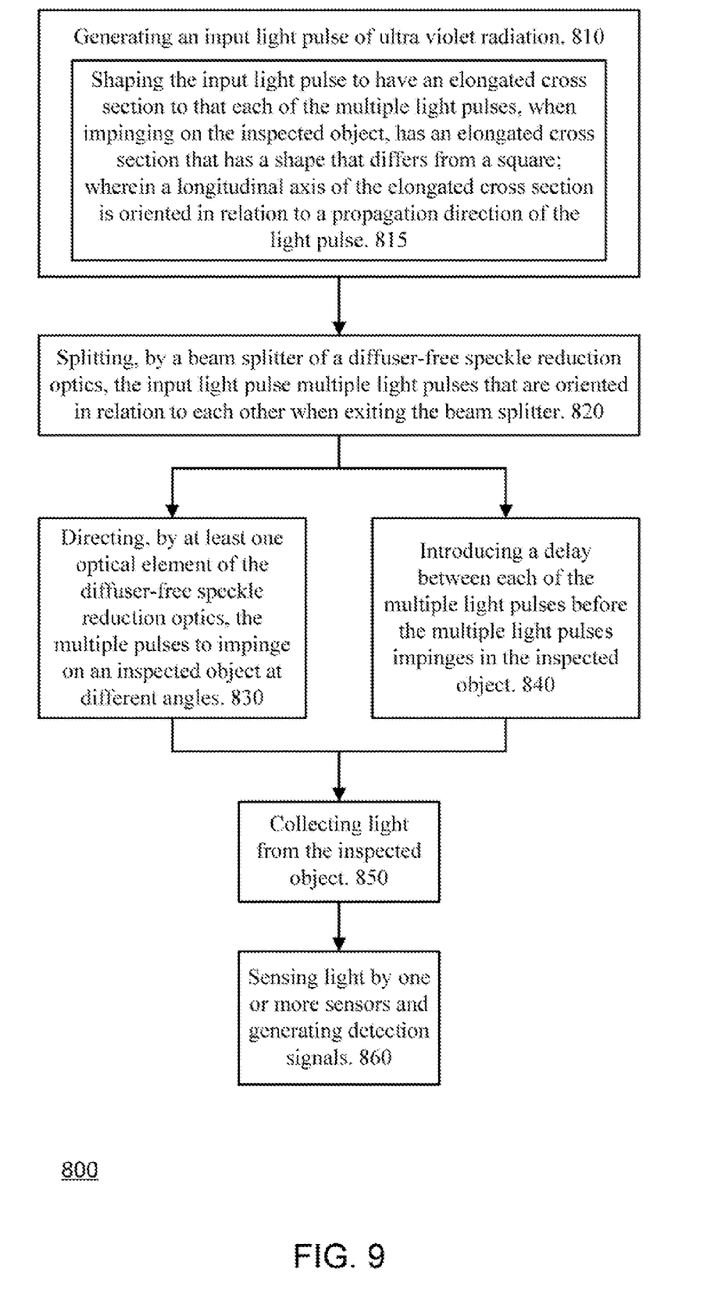
FIG. 9 is a flow chart of an inspection method according to an embodiment of the invention.

FIG. 9 illustrates a method 800 according to an embodiment of the invention.

Method 800 can be executed by any of the systems mentioned in connection with the previous figures.

Method 800 starts by step 810 of generating an input light pulse. The input pulse can be of ultra violet radiation but may be of another frequency.

Stage 810 is followed by step 820 of splitting, by to beam splitter of a diffuser-free speckle reduction optics, the input light pulse multiple light pulses that are oriented in relation to each other when exiting the beam splitter.

Stage 820 is followed by steps 830 and 840.

Step 830 includes directing, by at least one optical element of the diffuser-free speckle reduction optics, the multiple pulses to impinge on an inspected object at different angles.

Step 840 includes introducing a delay between each of multiple light pulses before the multiple light pulses impinges in the inspected object.

Stages 830 and 840 can occur in a sequential manner but this is not necessarily so. For example, referring to FIG. 1, the directing of the light pulses can be executed before the light pulses are delayed and also after they are being delayed by delay units 120 and 118.

Step 840 may include directing the multiple light pulses towards the inspected object while the multiple light pulses are located within an illumination angular zone.

Step 830 and 840 are followed by step 850 of collecting light. Step 850 may include collecting light that propagates through a collection angular zone that differs from the illumination angular zone.

Step 850 may be followed by step 860 of sensing light by one or more sensors and generating detection signals. Step 860 may include (or may be followed by) processing the detection signals (e.g., to create an image or images of the sample), storing the detection signals (e.g., for later processing) and the like.

Step 810 may include step 815 of shaping the input light pulse to have an elongated cross section so that each of the multiple light pulses, when impinging on the inspected object, has an elongated cross section that has a shape that differs from a square; wherein a longitudinal axis of the elongated cross section is oriented in relation to a direction of propagation of the light pulse. Additionally or alternatively, the beam shaping can be applied to the multiple light beams.

Step 840 can include introducing a delay that is longer that a width of the input light pulse.

Step 840 can include introducing a delay that is longer that a coherence length of the input light pulse.

Step 810 can include generating a single mode light pulse by a single mode laser.

Step 850 may include collecting scattered light from the inspected object. Step 850 may include collecting scattered light while not collecting reflected light from the inspected object.

Step 850 may include collecting light at a collection axis of collection optics. Wherein a projection of an illumination axis of a light pulse on the inspected object is oriented to a projection of the collection axis of the collection optics.

Step 820 can include splitting the input light pulse to an even or odd number of multiple light pulses.

This sequence of steps can be repeated for each input light pulse generated by a light source. An inspection of an inspected object usually involves generating a large number of input light pulses while introducing a mechanical movement between the inspected object and the collection module and the like so as to inspect a desired area of the sample. The inspection process can involve applying any known inspection algorithm, including die-to-die, die-to-reference (e.g., a stored reference image or one produced using a golden die), and the like. The inspection system and the inspection method can be applied mutatis mutandis to transmissive inspection during which radiation passes through the sample under inspection.

Figure 10:
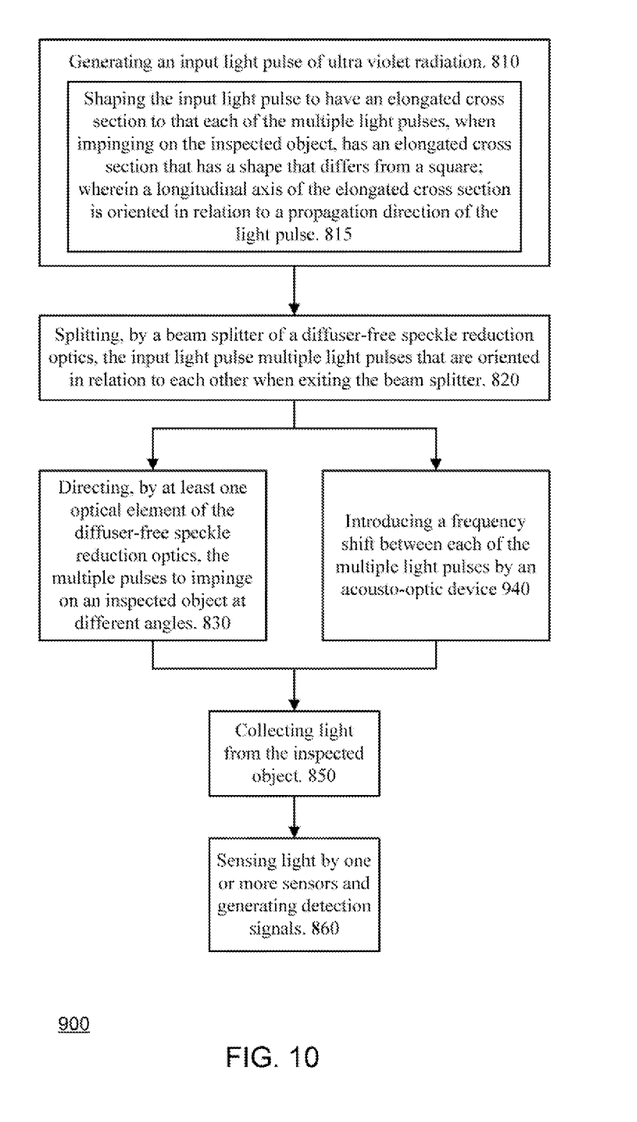
FIG. 10 is a flow chart of an inspection method according to am embodiment of the invention.

FIG. 10 illustrates a method 900 according to an embodiment of the invention.

Method 900 of FIG. 10 differs from method 800 of FIG. 9 by including step 940 of introducing a frequency shift between each of the multiple light pulses by an acousto-optic device, instead of step 840. Step 940 can include introducing a frequency shift by a beam splitter that is an acousto-optic device.

Step 940 can include modulating the acousto-optic device by a sinusoidal modulation signal so that the acousto-optic device introduces a frequency shift between the light pulses. The frequency shift can equal the frequency (wm) of the sinusoidal modulation signal. The frequency of a light pulse can increase by wm and a frequency of another light pulse can decrease by wm. Yet a frequency of another light pulse can be unchanged.

It is noted that method 800 or method 900 can include both steps 840 and 940.

It is noted that either one of methods 800 and 900 can include at least one additional step such as expanding the input light pulse, passing the input light pulse through a spatial filter, directing the multiple light pulses towards an opening of a beam stop and imaging the opening of the beam stop onto the inspected object—as is evident from FIGS. 2 and 4.

Figure 11:
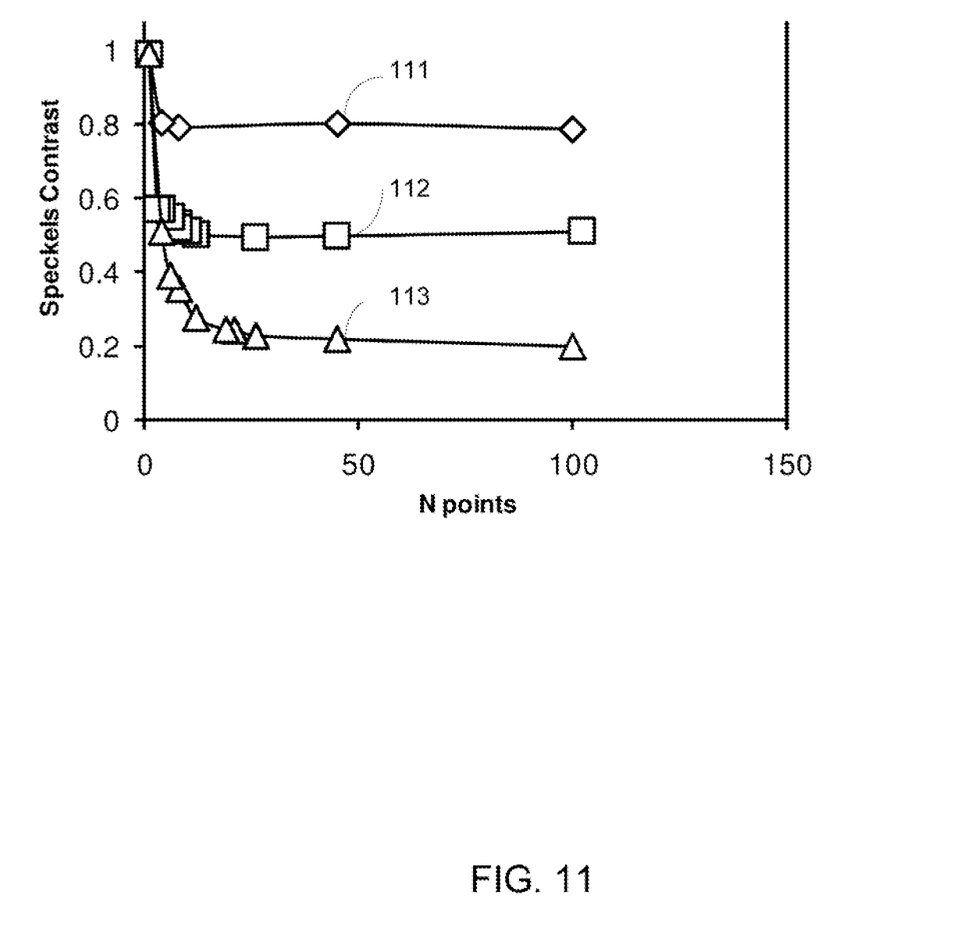
FIG. 11 illustrates a relationship between speckle contrast and the number of discrete light pulses that arrive at different angles, according to an embodiment of the in vent ion.

FIG. 11 illustrates a relationship between speckle contrast and the number of discrete light pulses that arrive at different angles, according to an embodiment of the invention.

FIG. 11 includes curves 111, 112 and 113. Each curve illustrates the relationship of the number of multiple light beams that impinge on an object (at different angles) and the speckle contrast for different values of sigma. Sigma is the relationship between the numerical aperture of illumination and the numerical aperture of collection. Lower sigma values result in higher speckle contrast.

Curve 111 illustrates the above-mentioned relationship for sigma=⅓, curve 112 illustrates the above-mentioned relationship for sigma=1, and curve 113 illustrates the above-mentioned relationship for sigma=3. These relationships are also illustrated in the following table:

| sigma | Number of light beams | Speckle contrast |
|---|---|---|
| 1 | 102 | 0.51 |
| 1 | 45 | 0.498 |
| 1 | 26 | 0.496 |
| 1 | 12 | 0.5013 |
| 1 | 10 | 0.51 |
| 1 | 8 | 0.533 |
| 1 | 8 | 0.522 |
| 1 | 6 | 0.549 |
| 1 | 4 | 0.57 |
| 1 | 3 | 0.57 |
| 1 | 1 | 0.99 |
| 0.333333 | 100 | 0.785 |
| 0.333333 | 45 | 0.8 |
| 0.333333 | 8 | 0.79 |
| 0.333333 | 4 | 0.803 |
| 0.333333 | 1 | 0.99 |
| 3 | 100 | 0.2 |
| 3 | 45 | 0.22 |
| 3 | 26 | 0.229 |
| 3 | 21 | 0.244 |
| 3 | 19 | 0.246 |
| 3 | 12 | 0.277 |
| 3 | 8 | 0.355 |
| 3 | 6 | 0.391 |
| 3 | 4 | 0.51 |
| 3 | 1 | 0.99 |

White certain features of the invention have been illustrated and described herein, many modifications, substitutions, changes, and equivalents will now occur to those of ordinary skill in the art. It is, therefore, to be understood that the appended clams are intended to cover it such modifications and changes as fall within the true spirit of the invention.

What is claimed is:

1. A system exhibiting speckle reduction characteristics, comprising:
   a light source arranged to generate light pulses, and diffuser-free speckle reduction optics that comprise:
      a beam splitter for receiving single mode light pulses from the light pulses generated by the light source and for splitting each single mode light pulse into multiple light pulses that are oriented at different angles in relation to each other when exiting the beam splitter; and at least one optical element for directing the multiple light pulses to impinge on an inspected object at different angles.

2. The system according to claim 1, wherein the at least one optical element comprises a delay module for introducing a delay between each of the multiple light pulses.

3. The system according to claim 2, wherein the delay module is arranged to introduce a delay that is longer than a width of the light pulses.

4. The system according to claim 2, wherein the delay module is arranged to introduce a delay that is longer than a coherence length of the light pulses.

5. The system according to claim 2, wherein the light source is a single mode laser.

6. The system according to claim 1, wherein the beam splitter is an acousto-optic device that is arranged to introduce a frequency shift between the multiple light pulses.

7. The system according to claim 6, wherein the beam splitter is an acousto-optic device that is modulated by a sinusoidal modulation signal.

8. The system according to claim 1, wherein each of the multiple light pulses, when impinging on the inspected object, has an elongated cross section that has a shape that differs from a square.

9. The system according to claim 8, wherein a longitudinal axis of the elongated cross section is perpendicular to a direction of propagation of at least one of the multiple light pulses.

10. The system according to claim 1, further comprising collection optics for collecting scattered light from the inspected object.

11. The system according to claim 10, further comprising a sensor that is arranged to receive scattered light while being prevented from receiving reflected light from the inspected object.

12. The system according to claim 10, wherein a projection of an illumination axis of the multiple light pulses on a plane defined by a surface of the inspected object is oriented at an angle to a projection of a collection axis of the collection optics.

13. The system according to claim 1, wherein the diffuser-free speckle reduction optics is arranged to direct different ones of the multiple light pulses, located within an illumination angular zone, towards the inspected object; and the system further comprises collection optics for collecting light that propagates through a collection angular zone that differs from the illumination angular zone.

14. The system according to claim 13, wherein the illumination angular zone is surrounded by the collection angular zone.

15. The system according to claim 1, wherein the multiple light pulses comprise an even number of light pulses.

16. The system according to claim 1, wherein the multiple light pulses comprise an odd number of light pulses.

17. The system according to claim 1, wherein the light pulses are ultra violet light pulses.

18. An inspection method, comprising:
generating a single mode light pulse;
splitting, by a beam splitter of a diffuser-free speckle reduction optics, the single mode light pulse into multiple light pulses that are oriented at different angles in relation to each other when exiting the beam splitter; and
directing, by at least one optical element of the diffuser-free speckle reduction optics, the multiple light pulses to impinge on an inspected object at different angles.

19. The inspection method according to claim 18, further comprising introducing a delay between each of the multiple light pulses before the multiple light pulses impinge on the inspected object.

20. The inspection method according to claim 18, further comprising introducing a frequency shift between each of the multiple light pulses by an acousto-optic device.

21. The inspection method according to claim 18, comprising shaping the single mode light pulse to have an elongated cross section so that each of the multiple light pulses, when impinging on the inspected object, has an elongated cross section that has a shape that differs from a square; wherein a longitudinal axis of the elongated cross section is oriented in relation to a direction of propagation of at least one of the multiple light pulses.

22. The inspection method according to claim 18, comprising directing the multiple light pulses towards the inspected object while the multiple light pulses are located within an illumination angular zone; and collecting light that propagates through a collection angular zone that differs from the illumination angular zone.

* * * * *